United States Patent
Klein et al.

(10) Patent No.: US 6,288,117 B1
(45) Date of Patent: Sep. 11, 2001

(54) METHOD FOR TREATING CONGESTIVE HEART FAILURE

(75) Inventors: Irwin Klein, Manhasset; Kaie Ojamaa, Glen Cove, both of NY (US)

(73) Assignee: North Shore-Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/533,227

(22) Filed: Mar. 23, 2000

(51) Int. Cl.$^7$ .................................................. A61K 31/195
(52) U.S. Cl. ................................................................ 514/567
(58) Field of Search ............................................... 514/567

(56) References Cited

U.S. PATENT DOCUMENTS

| | | | |
|---|---|---|---|
| 3,689,669 | * 9/1972 | Prange, Jr. et al. | 424/319 |
| 5,158,978 | 10/1992 | Rubin . | |
| 5,324,522 | * 6/1994 | Krenning et al. | 424/456 |

OTHER PUBLICATIONS

Beers and Berkow, eds. The Merck Manual of Diagnosis and Therapy, 17th ed. (Whitehouse Station, NJ: Merck Research Laboratories, 1999) 1682–91.
Katzeff et al., Alterations in cardiac contractility and gene expression during low–T3 syndrome: prevention with T3. Am. J. Physiol., E951–E956, 1997.
Klein et al., Potential clinical applications for parenteral thyroid hormone therapy. Hosp. Formul., 28:848–58, 1993.
Klein and Ojamaa, Editorial: Thyroid hormone and the cardiovascular system: from theory to practice, 78(5):1026–27, 1994.
Klein et al., Thyroid hormone and the heart. Am. J. Med., 101:459–60, 1996.
Klein and Ojamaa, Thyroid hormone and the cardiovascular system. Curr. Opin. Endocrin. & Diab., 341–46, 1997.
Klein and Ojamaa, Thyroid hormone treatment of congestive heart failure. Am. J. Cardiol., 81:490–91, 1998.
Klein and Ojamaa, Thyrotoxicosis and the heart. Endocrinol. Metab. Clin. North Am., 27(1):51–62, Mar. 1998.
Klemperer et al., Thyroid hormone treatment after coronary–artery bypass surgery. New Engl. J. Med., 333:1522–27, Dec. 1995.
Klemperer et al., Thyroid hormone therapy in cardiovascular disease. Progress in Cardiovascular Diseases, 38(4):329–36, Jan./Feb., 1996.
Levine, H.D., Compromise therapy in the patient with angina pectoris and hypothyroidism. Am. J. Med., 69:411–18, Sep. 1980.
Physicians' Desk Reference, 54th ed. (Montvale, NJ: Medical Economics Company, Inc., 2000) 1081–82, 1467, 1513.
Tereshchenko et al., Subclinical hypothyroidism in patients with ischemic heart disease. Kardiologiia, 33(11):45–7,5, 1993.
Wartofsky et al., Trading one "dangerous dogma" for another? Thyroid hormone treatment of the "euthyroid sick syndrome". JCEM, 84(5):1759–60, 1999.

* cited by examiner

*Primary Examiner*—Raymond Henley, III
(74) *Attorney, Agent, or Firm*—Amster, Rothstein & Ebenstein

(57) ABSTRACT

The present invention provides a method for chronic treatment of congestive heart failure (CHF) in a patient having CHF, by administering daily, over the long-term, an amount of $T_3$ effective to treat the CHF.

15 Claims, 1 Drawing Sheet

METHOD FOR TREATING CONGESTIVE HEART FAILURE

STATEMENT OF GOVERNMENT INTEREST

This invention was made with government support under NIH Grant No. HL-58849. As such, the United States government has certain rights in this invention.

BACKGROUND OF THE INVENTION

Congestive heart failure (CHF) is a common syndrome characterized by decreased cardiac contractility, abnormal diastolic compliance, reduced stroke volume, and pulmonary congestion, as well as decreased cardiac output. CHF may be caused by many different etiologies whose clinical manifestations reflect a decrease in the myocardial contractile state such that cardiac output is reduced. The CHF disease state may arise, for example, from deficiencies in cardiac contractility, right ventricular failure, biventricular failure, systolic dysfunction, diastolic dysfunction, and pulmonary effects. In particular, CHF develops when plasma volume increases and fluid accumulates in the lungs, abdominal organs, and peripheral tissues (Beers and Berkow, eds., *The Merck Manual of Diagnosis and Therapy*, 17$^{th}$ ed. (Whitehouse Station, N.J.: Merck Research Laboratories, 1999) 1682–88).

Drug treatment for CHF primarily involves diuretics, ACE inhibitors, digitalis, and β-blockers. In mild cases, thiazide diuretics, such as hydrochlorothiazide at 25–50 mg/day or chlorothiazide at 250–500 mg/day, are useful. However, supplemental potassium chloride is generally needed, since chronic diuresis causes hypokalemis alkalosis. Moreover, thiazide diuretics usually are not effective in patients with advanced symptoms of CHF. Typical doses of ACE inhibitors include captopril at 25–50 mg/day and quinapril at 10 mg/day. Numerous side effects are possible, though, including decreased blood pressure, renal insufficiency, potassium retention, and coughing. Digitalis preparations, particularly of digoxin, are widely prescribed in the United States, although the role of digitalis continues to be debated, and its usefulness in treating CHF in the absence of atrial fibrillation remains controversial. β-blockers, too, must be used with caution when treating patients with CHF. A more indirect component of CHF management includes the recognition and control of factors that may be causing increased cardiac demands or adversely affecting myocardial function (e.g., hypertension, anemia, excess salt intake, excess alcohol, arrhythmias, thyrotoxicosis, fever, increased ambient temperature, or pulmonary emboli) (Beers and Berkow, eds., *The Merck Manual of Diagnosis and Therapy*, 17$^{th}$ ed. (Whitehouse Station, N.J.: Merck Research Laboratories, 1999) 1688–91). In view of the foregoing, many of the current methods available for treating CHF produce negative side-effects, or are only indirect. Accordingly, there currently exists a need for new and better methods for improving the survival of patients with CHF.

Triiodothyronine ($T_3$) is a hormone synthesized in the thyroid gland. Along with tetraiodothyronine ($T_4$), $T_3$ is produced by the iodination and coupling of the amino acid tyrosine. $T_3$ is known to enhance oxygen ($O_2$) consumption by most tissues of the body, increase the basal metabolic rate, and influence the metabolism of carbohydrates, lipids, and proteins. While $T_4$ is commonly administered in replacement or supplemental therapy to treat patients with most forms of hypothyroidism, $T_3$ is only rarely administered because numerous complications are associated with its usage (as discussed below). In addition, $T_3$ is used as a pituitary thyroid-stimulating hormone (TSH) suppressant, in the treatment or prevention of various types of euthyroid goiters. Finally, $T_3$ is used as a diagnostic agent in suppression tests to differentiate suspected mild hyperthyroidism or thyroid gland autonomy (*Physicians' Desk Reference*, 54$^{th}$ ed. (Montvale, N.J.: Medical Economics Company, Inc., 2000) 1081, 1513).

Studies have also demonstrated that acute administration of $T_3$ can result in increased cardiac performance and reduced systemic resistance in a number of clinical scenarios, including cardiac transplantation, cardiopulmonary bypass (Klemperer et al., *N. Engl. J. Med.*, 333:1522–27, 1995), and myocardial ischemia (a deficiency of blood supply to the heart muscle, due to obstruction or constriction of coronary arteries) (Klein et al., *Hosp. Formul.*, 28:848–58, 1993). Nevertheless, it is well-recognized that thyroid-hormone therapy should be used with great caution in a number of circumstances where the integrity of the cardiovascular system, particularly the coronary arteries, is suspected (*Physicians' Desk Reference*, 54$^{th}$ ed. (Montvale, N.J.: Medical Economics Company, Inc., 2000) 1082, 1513).

Indeed, the long-term or chronic administration of $T_3$ has been historically contraindicated, due to concerns regarding oxygen-wasting effects, arrhythmia, and exacerbation of angina pectoris. In particular, the prevalent paradigm holds that $T_3$ is not suitable for long-term treatment, as it increases $O_2$ consumption by the heart without a concomitant increase in the blood supply: a classic scenario for the development of angina, fibrillation, and other heart conditions (Levine, H. D., *Am. J. Med.*, 69:411–18, 1980; Klemperer et al., *N. Engl. J. Med.*, 333:1522–27, 1995; and Klein and Ojamaa, *Am. J. Cardiol.*, 81: 490–91, 1998). H. D. Levine (*Am. J. Med.*, 69:411–18, 1980), for example, even suggested that the administration of thyroid hormone, and the return to a euthyroid state, would actually induce or exacerbate heart problems in patients with hypothyroidism and coronary disease.

The possible use of thyroid hormone to treat CHF was considered by Klein and Ojamaa in a review article (*Am. J. Cardiol.*, 81: 490–91, 1998). The suggestion was based predominantly on an earlier study in which a single high dose of thyroid hormone was administered to improve cardiac performance in an acute setting. No evidence was provided to indicate that long-term administration of $T_3$ could be successfully and safely used to treat CHF. The authors also expressly acknowledged that further research was necessary to ascertain the safety and efficacy of the use of $T_3$ to treat CHF. In view of the known contraindications associated with the long-term administration of $T_3$, the skilled artisan would not have had a reasonable expectation that $T_3$ could be used to safely treat CHF.

SUMMARY OF THE INVENTION

The present invention is predicated on the discovery that, contrary to the expectations in the prior art which teach away from the long-term $T_3$ administration, $T_3$ can successfully be used to treat CHF without producing deleterious effects. On the basis of this finding, the present invention provides a method for chronic treatment of congestive heart failure (CHF) by administering to the patient, over the long term, a daily dose of $T_3$.

Additional objects of the present invention will be apparent in view of the description which follows.

DETAILED DESCRIPTION OF THE INVENTION

Figure 1:
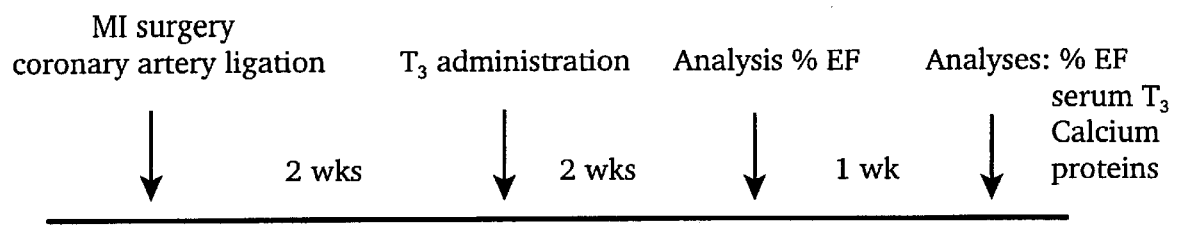
FIG. 1 depicts a time line for the experimental protocol utilized on animals in the present invention. As the figure illustrates, the animal's coronary artery was ligated by surgery, inducing myocardial infarction (MI). Two weeks later, $T_3$ administration was commenced. Two weeks after the commencement of $T_3$ administration, the percent ejection fraction (% EF) of the animal was measured in order to assess the function of the heart. One week later, % EF was again measured in the MI animal.

The present invention is directed to a method for chronic treatment of congestive heart failure (CHF) in a patient having CHF. The method of the present invention comprises the long-term administration to a patient of a daily dose of $T_3$ effective to treat CHF. The term "treat CHF", as used herein, means treating any one or more of the conditions underlying CHF, including, without limitation, decreased cardiac contractility, abnormal diastolic compliance, reduced stroke volume, pulmonary congestion, and decreased cardiac output, while minimizing or attenuating deleterious effects commonly associated with the long-term administration of $T_3$, such as oxygen-wasting effects, arrhythmias, and exacerbation of angina pectoris. As further used herein, "oxygen-wasting effects" include, without limitation, symptoms and signs of congestion due to increased ventricular filling pressures, and fatigue associated with low cardiac output.

As used herein, "long-term administration" means administration for at least three weeks. Furthermore, as used herein, "a daily dose" means the dose given within a 24-hour period. Additionally, as used herein, "$T_3$" refers to triiodothyronine and analogues thereof, including, for example, a functional variant of $T_3$ which has $T_3$ biological activity, as well as a fragment of $T_3$ having $T_3$ biological activity. As further used herein, the term "$T_3$ biological activity" refers to $T_3$ activity which improves myocardial contractility in a patient having CHF.

Synthetic $T_3$ is commercially available, and can be obtained from Jones Pharma Incorporated (St. Louis, Mo.). Liothyronine sodium is a synthetic preparation of $T_3$, and can be purchased in oral (Cytomel) and intravenous (Triostat) formulations. Cytomel tablets contain liothyronine (L-triiodothyronine), a synthetic form of a natural thyroid hormone, that is available as the sodium salt (*Physicians' Desk Reference*, 54th ed. (Montvale, N.J.: Medical Economics Company, Inc., 2000) 1467). A natural preparation of $T_3$ may be derived from animal thyroid. Natural preparations include desiccated thyroid and thyroglobulin. Desiccated thyroid is derived from domesticated animals that are used for food by humans (e.g., beef or hog thyroid), and thyroglobulin is derived from thyroid glands of the hog.

According to the method of the present invention, the amount of $T_3$ administered to a patient is a dose effective to treat CHF in a patient. It is an objective of the present invention to administer a dose of $T_3$ which will treat the conditions underlying CHF, including, without limitation, decreased cardiac contractility, abnormal diastolic compliance, reduced stroke volume, pulmonary congestion, and decreased cardiac output, while minimizing, attenuating or reducing deleterious effects commonly associated with the long-term administration of $T_3$, such as oxygen-wasting effects, arrhythmias, and exacerbation of angina pectoris. Preferably, the dose of $T_3$ is such that deleterious effects commonly associated with the long-term administration of $T_3$ are eliminated.

The method of the present invention may be used to treat a patient who is $T_3$-deficient, as well as a patient who is not $T_3$-deficient. However, it is preferable that $T_3$ be administered to a patient who is deficient in $T_3$. In such a patient, low doses of $T_3$, administered over the long term, would be expected to normalize, or slightly elevate above normal, serum $T_3$ levels in the patient, with minimal or no deleterious effects commonly associated with the long-term administration of $T_3$.

In the method of the present invention, $T_3$ is preferably administered chronically at a dose between about 5 µg/day and about 50 µg/day (i.e., between about 0.07 µg/kg/day and about 0.71 µg/kg/day). However, the actual dose will depend on the particular factors of each case, including the patient's weight and the severity of the patient's condition. Most preferably, $T_3$ is administered at a dose between about 15 µg/day and about 30 µg/day (i.e., between about 0.21 µg/kg/day and about 0.43 µg/kg/day). This amount of $T_3$ is extremely low compared to that required for acute treatment of heart failure patients and post-operation cardiac patients, for example, where $T_3$ is administered intravenously at a dose between 100 µg and 150 µg, over a 12-hour period.

According to the method of the present invention, the dose of $T_3$ is preferably administered daily for at least three weeks. The administration of $T_3$ may continue as long as the patient has symptoms of CHF and derives benefit from the administration of $T_3$. It is within the confines of the present invention that the $T_3$ be administered to the patient throughout his or her lifetime. The dose of $T_3$ may be administered to a human or animal patient by known procedures, including, but not limited to, oral administration, injection, transdermal administration, and administration through an osmotic mini-pump. Preferably, the dose of $T_3$ is administered orally.

For oral administration, the formulation of the dose of $T_3$ may be presented as capsules, tablets, powders, granules, or as a suspension. Preferably, the dose of $T_3$ is presented in a known sustained-release formulation, such that a single daily dose of $T_3$ may be administered. Specific sustained-release formulations are described in U.S. Pat. Nos. 5,885,616, 5,922,356, 5,968,554, 6,011,011, and 6,039,980, which are hereby incorporated by reference. The formulation of $T_3$ may have conventional additives, such as lactose, mannitol, corn starch, or potato starch. The formulation may also be presented with binders, such as crystalline cellulose, cellulose derivatives, acacia, corn starch, or gelatins. Additionally, the formulation may be presented with disintegrators, such as corn starch, potato starch, or sodium carboxymethyl-cellulose. Finally, the formulation may be presented with lubricants, such as talc or magnesium stearate.

For injection, the dose of $T_3$ may be combined with a sterile aqueous solution which is preferably isotonic with the blood of the patient. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be present in unit or multi-dose containers, such as sealed ampoules or vials. The formulation may be delivered by any mode of injection, including, without limitation, epifascial, intracutaneous, intramuscular, intravascular, intravenous, parenchymatous, or subcutaneous.

For transdermal administration, the dose of $T_3$ may be combined with skin penetration enhancers, such as propylene glycol, polyethylene glycol, isopropanol, ethanol, oleic acid, N-methylpyrrolidone, and the like, which increase the permeability of the skin to the dose of $T_3$, and permit the dose of $T_3$ to penetrate through the skin and into the bloodstream. The $T_3$/enhancer compositions may also be further combined with a polymeric substance, such as ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch.

The dose of $T_3$ of the present invention may also be released or delivered from an osmotic mini-pump. The release rate from an elementary osmotic mini-pump may be modulated with a microporous, fast-response gel disposed in the release orifice. An osmotic mini-pump would be useful for controlling release, or targeting delivery, of $T_3$.

The present invention is described in the following Experimental Details section, which is set forth to aid in the understanding of the invention, and should not be construed to limit in any way the scope of the invention as defined in the claims which follow thereafter.

Experimental Details

An animal model of myocardial infarction was used in the present studies to produce a model of CHF in which a decrease in serum $T_3$ could be demonstrated. This model was used to test the hypothesis that long-term, low-dose $T_3$ treatment could improve cardiac function. Analysis of the cardiac tissue was conducted to determine the molecular mechanisms by which this effect occurs.

Animals subjected to ligation of a coronary artery developed myocardial infarction (MI) and a decrease in function of the heart, as measured by the percent ejection fraction (% EF) (stroke volume/end-diastolic volume—normally>50%). As Table 1 shows, serum total $T_3$ levels in the MI animals fell by 40%, as compared with 56.58±8.35 ng/dl in the controls (C). This result was analogous to the decrease in serum total $T_3$ levels observed in humans. In the MI animals, % EF decreased by 47% over 14 and 21 days after surgery (Table 2).

TABLE 1

Serum total $T_3$ and total $T_4$ in control (C) rats, myocardial infarcted (MI) rats, and MI rats treated with $T_3$ (MI + $T_3$)

|  | N | $T_3$ (ng/dl) | $T_4$ (µg/dl) |
|---|---|---|---|
| C | 7 | 56.58 ± 8.35 | 6.60 ± 0.48 |
| MI | 6 | 34.76 ± 5.24* | 6.15 ± 0.22 |
| MI + $T_3$ | 5 | 59.75 ± 5.29 | 3.85 ± 1.19** |

*$p < 0.05$ vs. C and MI + $T_3$
**$p < 0.05$ vs. C and MI $T_3$ was administered by continuous subcutaneous infusion to a subset of the MI animals, 2 weeks after coronary artery ligation surgery (FIG. 1). At the low-dose $T_3$ treatment regimen, measurements of serum total $T_3$ levels were restored to normal values at the termination of the experiment (Table 1). At the same time, serum $T_4$ levels fell, reflecting the expected effect of $T_3$ on the pituitary-thyroid axis (Table 1). As Table 2 shows, $T_3$ treatment produced a time-dependent increase in % EF in the MI animals (MI+ $T_3$), and returned left ventricular function to 80% of control (C) animals (65±2 vs. 82±2% EF), as compared with 59% of controls in the untreated MI animals.

TABLE 2

Effects of $T_3$ treatment on ejection fractions (% EF) of rats with myocardial infarction (MI)
% EF measured by M-mode echo Days of $T_3$ treatment following MI

|  | N | 14 d | 21 d |
|---|---|---|---|
| C | 5 | 80 ± 2 | 82 ± 2 |
| MI | 4 | 43 ± 2* | 49 ± 3* |
| MI + $T_3$ | 4 | 53 ± 5* | 65 ± 2** |

*$p < 0.01$ vs. C
**$p < 0.05$ vs. MI

Cardiac contractility is primarily regulated by the calcium cycling proteins: sarcoplasmic reticulum (SR) calcium-ATPase (SERCA2) and phospholamban (PLB). $T_3$ is known to regulate these proteins in normal hearts. As Table 3 shows, chronic subcutaneous administration of $T_3$ increased SERCA2 protein content in MI hearts, and altered the ratio of SERCA2 to PLB in a direction that can account for the increase in % EF. In addition, $T_3$ treatment of MI animals altered the PLB phosphorylation state (1.6 vs. 1.0 PLB-phos/unphos), which is also an established mechanism to enhance contractility of the heart.

Based on the above data, it may be concluded that chronic $T_3$ treatment can be proposed as a therapy for improvement of cardiac function in a variety of disease states, including CHF.

TABLE 3

Western analysis of SR calcium-ATPase and phospholamban in response to myocardial infarction (MI) and $T_3$ treatment (MI + $T_3$)

|  | N | SERCA2 | PLB | SERCA2/PLB | PLB-(phos/unphos) |
|---|---|---|---|---|---|
| C | 4 | 2.57 ± 0.28 | 20.8 ± 2.2 | 0.145 ± 0.03 | 1.1 |
| MI | 4 | 2.47 ± 0.28 | 15.1 ± 1.1 | 0.168 ± 0.03 | 1.0 |
| MI + $T_3$ | 5 | 3.19 ± 0.69 | 14.6 ± 1.4* | 0.284 ± 0.08** | 1.6** |

*$p < 0.005$ vs. C and MI
**$p < 0.05$ vs. C

All publications mentioned hereinabove are hereby incorporated in their entirety. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for treating congestive heart failure (CHF) in a patient having CHF, comprising the long-term administration to the patient an amount of $T_3$ effective to treat CHF in the patient.

2. The method of claim 1, wherein $T_3$ is administered daily.

3. The method of claim 1, wherein $T_3$ is administered at a dose between about 5 µg/day and about 50 µg/day.

4. The method of claim 1, wherein $T_3$ is administered at a dose between about 15 µg/day and about 30 µg/day.

5. The method of claim 1, wherein $T_3$ is administered for at least three weeks.

6. The method of claim 1, wherein $T_3$ is administered orally.

7. The method of claim 1, wherein $T_3$ is administered once daily in a sustained-release formulation.

8. A method for treating congestive heart failure (CHF) in a patient having CHF, comprising the long-term administration to the patient of an amount of $T_3$ effective to treat CHF in the patient, wherein $T_3$ is administered daily at a dose between about 5 μg/day and about 50 μg/day.

9. The method of claim 8, wherein $T_3$ is administered for at least three weeks.

10. The method of claim 8, wherein $T_3$ is administered orally.

11. The method of claim 8, wherein $T_3$ is administered once daily, in a sustained-release formulation.

12. A method for treating congestive heart failure (CHF) in a patient having CHF, comprising the long-term administration to the patient of an amount of $T_3$ effective to treat CHF in the patient, wherein $T_3$ is administered daily at a dose between about 15 μg/day and about 30 μg/day.

13. The method of claim 12, wherein $T_3$ is administered for at least three weeks.

14. The method of claim 12, wherein $T_3$ is administered orally.

15. The method of claim 12, wherein $T_3$ is administered once daily in a sustained-release formulation.

* * * * *